US00PP30329P2

(12) United States Plant Patent
Tures et al.

(10) Patent No.: US PP30,329 P2
(45) Date of Patent: Apr. 2, 2019

(54) ***VIBURNUM* PLANT NAMED 'FIT 2B TIED'**

(50) Latin Name: *Viburnum carlesii*
Varietal Denomination: Fit 2B Tied

(71) Applicant: Grateful Grower, Woodstock, IL (US)

(72) Inventors: Jeff Tures, Harvard, IL (US); Nancy Tures, Woodstock, IL (US)

(73) Assignee: Nancy Tures, Woodstock, IL (US)

( * ) Notice: Subject to any disclaimer, the term of this patent is extended or adjusted under 35 U.S.C. 154(b) by 0 days.

(21) Appl. No.: 15/732,841

(22) Filed: Jan. 4, 2018

(51) Int. Cl.
*A01H 5/00* (2018.01)

(52) U.S. Cl.
USPC ..... Plt./226

(58) Field of Classification Search
USPC ..... Plt./226
See application file for complete search history.

*Primary Examiner* — Annette H Para
(74) *Attorney, Agent, or Firm* — Penny J. Aguirre

(57) ABSTRACT

A new cultivar of *Viburnum carlesii* plant named 'Fit 2B Tied' that is characterized by its stems that are flexible and not easily broken and can be readily tied up as a ball and burlap plant for transport, its medium plant size and mounded plant habit, its clusters of flowers that are whitish pink in color and open from red buds, and its fall foliage that is red in color.

2 Drawing Sheets

Botanical classification: *Viburnum carlesii.*
Variety denomination: 'Fit 2B Tied'.

BACKGROUND OF THE INVENTION

The present invention relates to a new and distinct cultivar of *Viburnum carlesii*. The new *Viburnum* will hereafter by its cultivar name, 'Fit 2B Tied'. 'Fit 2B Tied' represents a new cultivar of Korean spice *viburnum* grown for use as an ornamental landscape plant.

'Fit 2B Tied' was discovered by the Inventors as a chance seedling in a production field in Huntley, Ill. in summer of autumn of 1987. The parent plants are therfore unknown.

Asexual propagation of the new cultivar was first accomplished by one of the Inventors using softwood stem cuttings in June of 2005 in Alden, Ill. Asexual propagation by softwood stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Fit 2B Tied' as a unique cultivar of *Viburnum.*

1. 'Fit 2B Tied' exhibits stems that are flexible and not easily broken and can be readily tied up as a ball and burlap plant for transport.
2. 'Fit 2B Tied' exhibits a medium plant size and mounded plant habit.
3. 'Fit 2B Tied' exhibits clusters of flowers that are whitish pink in color and open from red buds.
4. 'Fit 2B Tied' exhibits fall foliage that is red in color.

'Fit 2B Tied' can be compared to typical plants of *Viburnum carlesii*, which are similar to 'Fit 2B Tied' in flower fragrance and fall foliage coloration. Typical plants of *Viburnum carlesii* differ from 'Fit 2B Tied' in having a faster growth rate, flowers that are larger in size and stems that are less flexible and break when tied up. 'Fit 2B Tied' can also be compared to *Viburnum carlesii* cultivar 'Compactum' (not patented). 'Compactum' is similar to 'Fit 2B Tied' in flower fragrance and fall foliage coloration. 'Compactum' differs from 'Fit 2B Tied' in having a faster growth rate, flowers that are larger in size, stems that are less flexible, and a more compact plant habit.

BRIEF DESCRIPTION OF THE DRAWINGS

The accompanying colored photographs illustrate the overall appearance and distinct characteristics of the new cultivar. The plant in the photographs is about 20 years in age as grown outdoors in a trial garden in Alden, Ill.

The photograph in FIG. 1 provides a side view of 'Fit 2B Tied' in bloom.

Figure 1:
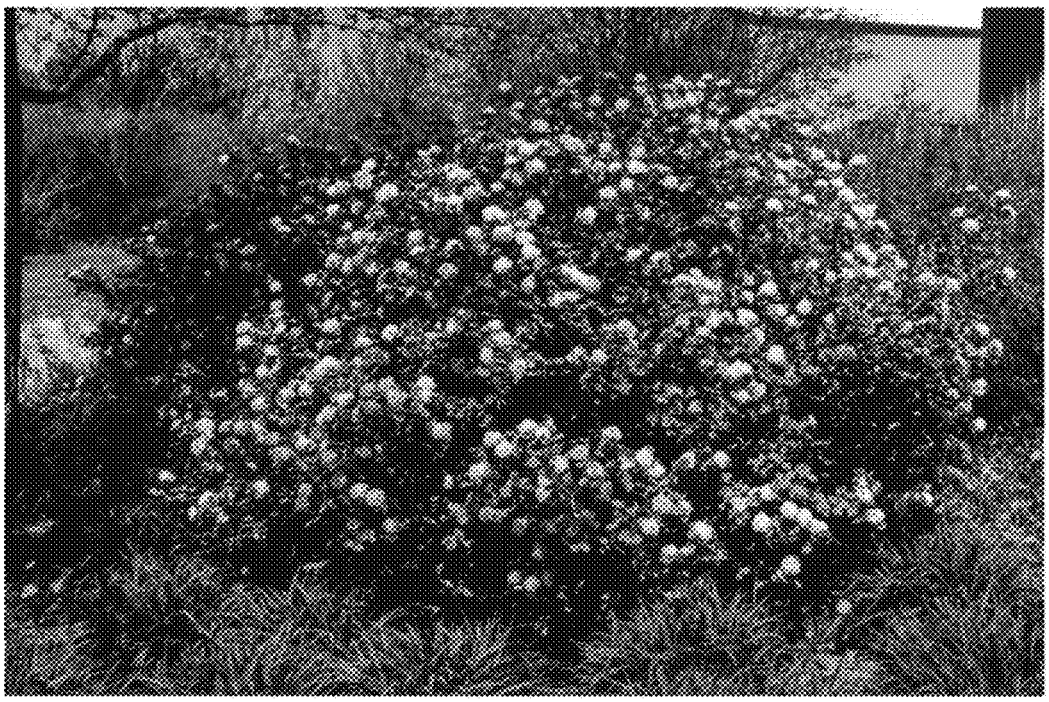
Figure 2:
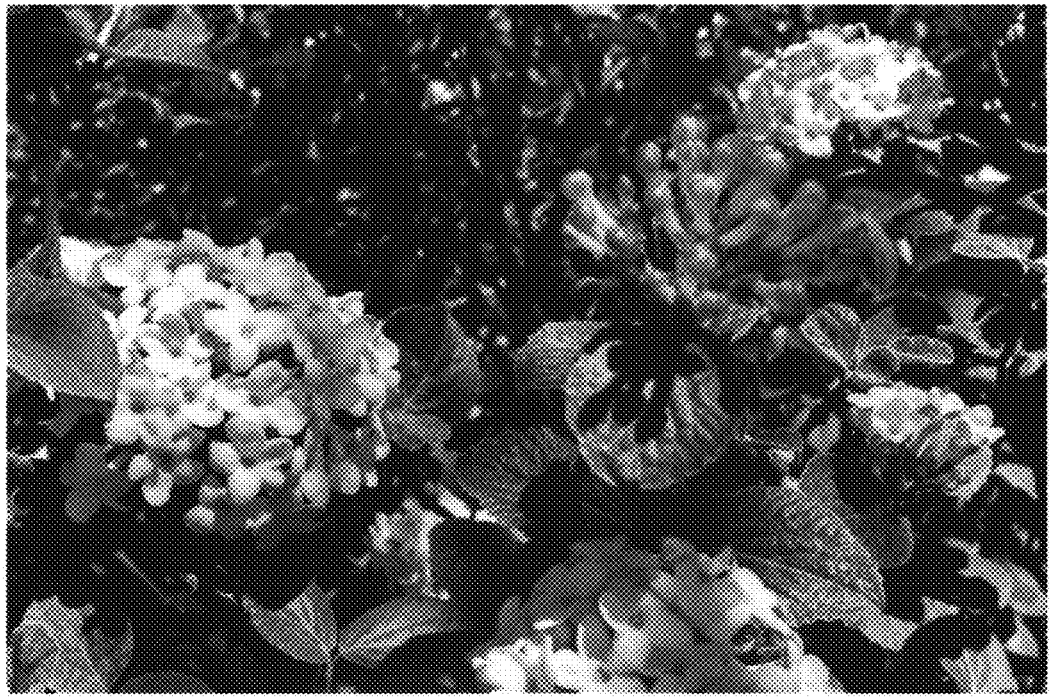

The photograph in FIG. 2 provides a close-up view of the flower buds and inflorescences of 'Fit 2B Tied'.

Figure 3:
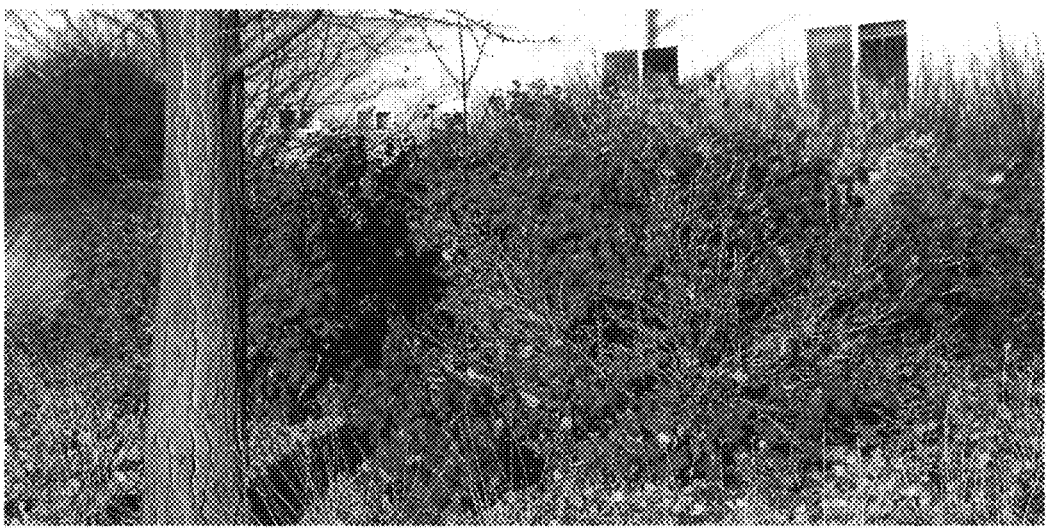

The photograph in FIG. 3 provides a view of the fall foliage of 'Fit 2B Tied'.

The colors in the photograph may differ slightly from the color values cited in the detailed botanical description, which accurately describe the colors of the new *Viburnum.*

DETAILED BOTANICAL DESCRIPTION

The following is a detailed description of 3 year-old plants of the new cultivar as grown outdoors in a 4-inch container in Huntley, Ill. and mature size and other general characteristics provided from a plant 20 years in age as field grown in Huntley, Ill. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period*.—Blooms mid June, blooming for an average of 2 to 4 weeks (weather dependent) in Huntley, Ill.

*Plant type*.—Deciduous shrub.

*Plant habit*.—Medium sized, freely branched, and mounded.

*Plant size*.—An average of 9 cm in height and 16 cm in spread in a 4-inch container, average of 1.88 m in height and 1.52 m in width in the landscape as a mature plant in the landscape.

*Cold hardiness*.—At least in U.S.D.A. Zone 4.

*Diseases*.—No resistance or susceptibility to diseases has been observed.

*Root habit*.—Dense, freely branching and between 200A and 200B in color.

*Root development*.—Roots initiate in 5 days and 5 to 6 years to produce a plant 18-inch in height in the field.

*Propagation*.—Softwood stem cuttings.

*Growth rate*.—Slow.

Branch description:

*Branch shape*.—Rounded.

*Branch color*.—Young branches; a blend of 197A and 177A, mature branches; a blend of N199C and 199D.

*Branch size*.—Plant in 4-inch container; 10 cm in length and 3 mm in diameter.

*Branch surface*.—Young stems densely covered with puberulent hairs, rough to the touch, too small to measure length, matching branch color, mature stems smooth and glabrous.

*Branch strength*.—Strong.

*Branching*.—Average of 1 main branch, 2 lateral branches, 2 tertiary branches per lateral branch.

*Internode length*.—Average of 1.5 cm.

Foliage description:

*Leaf shape*.—Ovate.

*Leaf division*.—Single.

*Leaf base*.—Rounded.

*Leaf apex*.—Acute.

*Leaf fragrance*.—None.

*Leaf venation*.—Pinnate, color varies between matching leaf color and 195A in color.

*Leaf margins*.—Serrate.

*Leaf arrangement*.—Opposite.

*Leaf attachment*.—Petiolate.

*Leaf surface*.—Both surfaces pubescent, upper surface rough to the touch densely covered with puberulent hairs, too small to measure length, N167 in color, lower surface soft to the touch and densely covered with tomentose matted hairs; too small to measure length, color matches leaf surface.

*Leaf size*.—An average of 7 cm in length and 6 cm in width.

*Leaf quantity*.—An average of 17 per plant in a 4-inch container.

*Leaf color*.—New growth upper surface; 146A, new growth lower surface; a blend of 152A and 146A, mature growth upper surface; a color between 137A and 147A, mature growth lower surface; a color between 147B and 147C, fall color; upper and lower surface a blend of 46A, 45C and 53A.

*Dormant leaf buds*.—Average of 6 mm in length and 2 mm in width, oblong in shape, densely puberulent surface, N200A.

*Petioles*.—Average of 7 mm in length and 2 mm in diameter, upper surface; glabrous, 146A in color, lower surface; densely pubescent, 0.5 mm in length and matches leaf surface.

Flower description:

*Inflorescence type*.—Terminal cluster.

*Lastingness of inflorescence*.—2 weeks to 4 weeks depending on weather conditions.

*Inflorescence size*.—Average of 3 cm in height and 6.5 cm in diameter.

*Inflorescence number*.—One per tertiary branch.

*Flower number*.—An average of 60 flowers per inflorescence.

*Flower fragrance*.—Strong, very fragrant.

*Flower aspect*.—Upright and outward.

*Flower size*.—An average of 1.7 cm in diameter and height.

*Flower type*.—Salviform.

*Flower buds*.—An average of 1.5 cm in length and 5 mm in diameter, oblong to linear in shape, N57A, heavily flushed with 161C in color, surface glabrous with bract portion pubescent.

*Peduncles*.—Strong in strength, average of 8 mm in length and 2 mm in width, 146C in color, surface is stellate pubescent with hairs 163D in color, held at various angles to stem.

*Pedicels*.—2 to 3 flowers held on one pedicel, Strong, an average of 3 mm in length and 1 mm in width, 146D in color, surface is stellate pubescent with hairs 163D in color, held at various angles to peduncle.

*Petals*.—5 in a single whorl, fused at base in tube, lobes; ovate in shape, margin entire and slightly undulating, broadly acute to rounded apex, both surfaces smooth, 6 mm in length and width, color upper surface when opening and fully open; NN155D, color of lower surface when opening and fully open; NN155D and irregular suffused with 63B to 63C, tube; average of 9 mm in length and 3 mm in width, NN155D in color on inner and outer surfaces, glabrous and smooth on inner and outer surfaces.

*Calyx*.—Elongated campanulate in shape, an average of 5 mm in length an 2 mm in width (at apex), comprised of 5 fused sepals with tips spreading, free tips: 0.7 mm in length and width, acute apex, 146B in color with very margins 178C in color, irregularly serrated margins, glabrous and satiny on both surfaces, tube; 4 mm in length and 1.5 mm in width, 146B in color on both surfaces with outer surface suffused with 178C, both surfaces glabrous and satiny.

*Bracts*.—Average of 2 per flower, lanceolate in shape, entire and pubescent margins, acute apex, truncate base, both surfaces pubescent, 4 mm in length, 1.5 mm in width, color of inner and outer surfaces 146D and suffused towards apex with 178C, slightly curved inward.

Reproductive organs:

*Stamens*.—Average of 5, anther; is 2 mm in length, oblong in shape, 160B in color, filament; an average of 7 mm in length, translucent and 157A in color with very slightly flush of 62C, pollen is moderate in quantity and 14C in color.

*Pistils*.—Average of 1, average of 2 mm in length, style is stout and an average of 1.7 mm in length and 1.5 mm in width and 144B in color, stigma is 3-branched, round in shape, <0.5 mm in diameter and 187C in color, ovary is partially inferior and 144C in color.

*Seed and fruit*.—Have not been observed to date.

What is claimed is:

1. A new and distinct cultivar of *Viburnum* plant named 'Fit 2B Tied' as herein illustrated and described.

* * * * *